United States Patent [19]

Bages et al.

[11] Patent Number: 5,740,073
[45] Date of Patent: Apr. 14, 1998

[54] LUBRICANT PROPERTY DETERMINATION

[75] Inventors: Sylvie Bages, Lavera; Bernard Descales, Marseilles; Didier Lambert, Saint-Mitre-Les-Remparts; Jean-Richard Llinas, Marseilles; Andre Martens, Chateauneuf-Les-Martigues, all of France

[73] Assignees: BP Chemicals Limited; BP Oil International Limited, both of London, England

[21] Appl. No.: 465,920

[22] Filed: Jun. 6, 1995

[30] Foreign Application Priority Data

Oct. 7, 1994 [EP] European Pat. Off. ............ 94430012

[51] Int. Cl.$^6$ .................... G01N 31/08; G06F 15/42
[52] U.S. Cl. .................... 364/499; 364/498; 364/500
[58] Field of Search .................... 364/496, 497, 364/498, 499, 500, 571.01, 578; 250/343, 339; 585/501, 613

[56] References Cited

U.S. PATENT DOCUMENTS

| | | | |
|---|---|---|---|
| 3,896,312 | 7/1975 | Brown et al. | 250/343 |
| 3,997,786 | 12/1976 | Lauer et al. | 250/343 |
| 4,251,870 | 2/1981 | Jaffe | 364/500 |
| 4,766,551 | 8/1988 | Begley | 364/498 |
| 4,882,755 | 11/1989 | Yamada et al. | 381/41 |
| 5,023,804 | 6/1991 | Hoult | 364/498 |
| 5,082,985 | 1/1992 | Crouzet et al. | 585/501 |
| 5,121,337 | 6/1992 | Brown | 364/498 |
| 5,153,140 | 10/1992 | Langfeld et al. | 436/55 |
| 5,225,679 | 7/1993 | Clarke et al. | 250/343 |
| 5,262,961 | 11/1993 | Farone | 364/500 |
| 5,311,445 | 5/1994 | White | 364/498 |
| 5,361,912 | 11/1994 | Krieg et al. | 209/524 |
| 5,446,681 | 8/1995 | Gethner et al. | 364/498 |
| 5,452,232 | 9/1995 | Espinosa et al. | 364/498 |
| 5,475,612 | 12/1995 | Espinosa et al. | 364/499 |

FOREIGN PATENT DOCUMENTS

| | | |
|---|---|---|
| 0305090A2 | 11/1988 | European Pat. Off. ........... 364/498 |
| 304232 | 2/1989 | European Pat. Off. . |
| 305090 | 3/1989 | European Pat. Off. . |
| 345182 | 12/1989 | European Pat. Off. . |

(List continued on next page.)

OTHER PUBLICATIONS

"Near-Infrared Spectrum Qualification via Mahalanobis Distance Determination" (*Applied Spectroscopy*; vol. 41, No. 7; R. G. Whitfield et al.; pp. 1204–1213; ©1987).

"Unique Sample Selection via Near-Infrared Spectral Subtraction" (*Analytical Chemistry*; vol. 57; No. 12; D. E. Honigs et al.; pp. 2299–2303; ©1985).

(List continued on next page.)

*Primary Examiner*—Emanuel T. Voeltz
*Assistant Examiner*—Bryan Bui
*Attorney, Agent, or Firm*—Fay, Sharpe, Beall, Fagan, Minnich & McKee

[57] ABSTRACT

A method of determining or predicting a value $P_x$ of a property of a material X, which is a feed to a process or a property of a product of a process from said material or yield of said process, which method comprises measuring the absorption $D_ix$ of said material at more than one wavelength in the region 600–2600 nm, comparing the said absorptions or a derivative thereof with absorptions $D_im$ or derivatives thereof at the same wavelength for a number of standards S in a bank for which said property or yield P is known, and choosing from the bank at least one standard $S_m$ with property $P_m$ said standard having the smallest average value of the absolute difference at each wavelength i between the absorption $D_ix$ (or derivative thereof) for the material and the absorption $D_im$ (or derivative thereof) for the standard $S_m$ to obtain $P_x$, with averaging of said properties or yields $P_m$ when more than one standard $S_m$ is chosen, and wherein said material X is a composition comprising part of a lubricating oil fraction obtainable from a vacuum distillation of oil.

28 Claims, 1 Drawing Sheet

FOREIGN PATENT DOCUMENTS

| | | |
|---|---|---|
| 437829 | 7/1991 | European Pat. Off. . |
| 607048 | 7/1994 | European Pat. Off. . |
| 625702 | 11/1994 | European Pat. Off. . |
| 631810 | 1/1995 | European Pat. Off. . |
| 2626579 | 8/1989 | France . |
| WO92/07326 | 4/1992 | WIPO . |
| WO93/20429 | 10/1993 | WIPO . |
| WO94/08226 | 4/1994 | WIPO . |

OTHER PUBLICATIONS

"Selection of Calibration Samples for Near–Infrared Spectroscopy by Factor Analysis of Spectra" (*Analytical Chemistry*; vol. 60, No. 6; G. Puchwein; pp. 569–573; ©1988.

"Selection of Samples for Calibration in Near–Infrared Spectroscopy. Part II: Selection Based on Spectral Measurements" (*Applied Spectroscopy*; vol. 44, No. 7; T. Isaksson and T. Naes; pp. 1152–1158; ©1990.

"The Design of Calibration in Near Infra–Red Reflectance Analysis by Clustering" (*Journal of Chemometrics*; vol. 1; T. Naes; pp. 121–126; ©1987.

"Computer Searching of Infrared Spectra Using Peak Location and Intensity Data" (*Analytical Chem.*; vol. 48; No. 4; R. C. Fox; pp. 717–721; ©1976.

"On–line NIR Analysis and Advanced Control Improve Gasoline Blending" (*Oil Gas J.*; vol.92; No.42; A. Espinosa et al.; pp. 49–56; ©1994).

"Online Process Analyzers" (*Chemical Engineering*; vol. 83; No. 13; V. C. Utterback; pp. 141–144; ©1976).

"Nonlinear Multicomponent Analysis by Infrared Spectrophotometry"; *Analytical Chemistry*; vol. 55; M. Maris and C. Brown; pp. 1624–1702; ©1983.

"Multicomponent Analysis of FT–IR Spectra"; *Applied Spectroscopy*; vol. 45, No. 6; P. Saarinen and J. Kauppinen; pp. 953–963; ©1991.

LUBRICANT PROPERTY DETERMINATION

This invention relates to a method of determining or predicting by near infra red (NIR) spectroscopy properties of feeds or products and/or yields in processes involving hydrocarbon, for lubricant uses.

NIR spectroscopy has many advantages over other methods of analysis in refineries and can cover a large number of repetitive applications accurately, quickly and on line. The NIR region between 800 and 2500 nm contains the totality of molecular information in the form of combinations and overtones from polyatomic vibrations, but Mathematical techniques are needed to exploit this information and to calculate the desired parameters. EP-A-285251, 304232, 305090, the disclosure of which is hereby incorporated by reference, describe the use of NIR for determining octane number, yields and/or properties of a product of a chemical process or separation process from analysis on the feeds to that process, and yields and/or properties of a product of a blending operation again from analysis on the feed thereto.

At present, numerical methods described for modelling physicochemical properties based on NIR spectra all are of a correlative nature and involve relations of a regressional character between the property(ies) studied. Among these multivariable analyses are multilinear regression (MLR), Principle Component Regression (PLR), Canonic regression, and regression by Partial Least Squares (PLS). In all cases there is sought between the property and the NIR spectrum a relation which may be linear but is usually quadratic or of higher algebraic form involving regression coefficients applied to each absorption. The establishment of any regression requires a progressive calibration, as the approach is empirical and not supported by a theory.

These techniques have disadvantages, the chief of which is the need for establishing a strong correlation between the spectrum and the property, and their difficulty in dealing with positive or negative synergy between components contributing to that property. Furthermore there are other practical difficulties mainly in the need to identify sample families having the same kind of relation between the spectra and the properties to be modelled. Thus the model may be limited especially with a non linear relation between spectrum and property. Especially when at the edges of the available data the accuracy of the model diminishes. The stability of the model is also a problem, as is the need when adding new standards to do laborious revisions to give the new model, especially when adjusting to a new feedstock for a process; thus testing 6 properties on 4 products leaving a process requires 24 models, each of which has to be changed for each change of the feed not included in the calibration.

We have discovered a new approach avoiding the above problems with correlations, and regression calculations, and being capable of being expanded automatically with use of a new product of different quality.

The present invention provides a method of determining or predicting a value $P_x$, of a property of a material or a property of a product of a process from said material or yield of said process which method comprises measuring the absorption ($D_i x$) of said material at more than one wavelength in the region 600–2600 nm, comparing the said absorptions or a derivative thereof with absorptions ($D_i m$) or derivatives thereof at the same wavelengths for a number of standards S in a bank for which the said property or yield P is known, and choosing from the bank at least one, preferably at least 2 standard $S_m$ with property $P_m$ having the smallest average value of the absolute difference at each wavelength i between the absorption $D_i x$ (or derivative thereof) for the material and the absorption $D_i m$ (or derivative thereof) for the standard $S_m$ to obtain $P_m$ with averaging of said properties or yields Pm when more than 1 standard $S_m$ is chosen and wherein said material X is a composition comprising part of a lubricating oil fraction obtainable from a vacuum distillation of oil.

The above method can be performed without regression or correlation techniques.

Thus for the performance of the method of the invention, a bank is prepared in which the NIR spectra are recorded at many wavelengths for a large number of standard materials, together with their properties determined by alternative techniques e.g. viscosities by known mechanical methods. The standards are chosen to cover the area in which the method is to be used, so for viscosity determination a range of base oils is chosen of widely varying viscosities. The number of wavelengths chosen may be 2–1000 e.g. 5–200 or 10–80 such as 40–70 while the number of standards can be at least 100 or 1000, or 100,000 up to 5 million depending on property(ies) chosen.

The wavelengths chosen may be at regular intervals such as each 1–50 or 15–35 nm or each 1–5 nm or each nanometer or may be at irregular intervals e.g. with spacings of 1–100 nm e.g. 2–50 nm, which may be random or chosen because of a change in the shape of the spectral curve at that wavelength e.g. a peak, trough or shoulder. The wavelengths may be in the region 600–2600 nm, eg 1000–2500 nm but preferably 1500–2600 such as 2000–2550 nm while the wavenumbers may be 16,600–3840 cm$^{-1}$ e.g. 10,000–4,000, e.g. 6,660–3840 cm$^{-1}$ or 5000–3900 cm$^{-1}$. Frequencies in Hertz are obtained by multiplying the wavenumbers by $3\times10^{10}$ cm/sec.

The absorptions for the unknown sample are compared with the absorptions at the same wavelength of the standards, and those standards chosen having the smallest differences. The properties of those chosen standards are then averaged to determine the property of the unknown sample. The absorptions at more than one wavelength may be chosen, e.g. 2–1000 such as 5–100 or 10–20.

In the method of the invention the standards chosen are those with the smallest average values of the absolute difference at each wavelength i between the absorption/optical density (or a derivative thereof) $D_{ix}$ for the unknown material and the corresponding absorption/optical density (or derivative thereof) $D_{im}$ for the standard. The averages may be in respect of the mean value of $D_{ix}-D_{im}$, (whatever its sign ie the absolute value) or $(D_{ix}-D_{im})^2$ and may be the simple mean value or the differences may be weighted to take account of the different sensitivity of the absorption to the property at that wavelength or the different sensitivity of the spectrometer at that wavelength. For each standard in the bank of standards for the type of material in question, the average difference is found as described and the standards with the smallest average differences chosen, e.g. at least 1 but preferably at least 2 such as up to 1000 smallest such as 1 or 2–100 or 1 or 2–20, but in particular 1 or 2–10 and especially 2–6 smallest. Advantageously the average differences chosen and hence the standard (or standards) $S_m$ chosen for the property or yield wanted are such that in relation to the unknown material X and each chosen standard $S_m$ the following function is met $$i_{xm}/\Sigma D_{ix} < \text{experimental error}$$

wherein $i_{xm}$ is the proximity index and is defined by $i^2(_{xm}) = \Sigma(D_{ix}-D_{im})^2$ and the experimental error is in determining said property or yield in the standard. The value $P_x$ of the property or yield is the same as $P_m$, or the average Pm if more than one standard $S_m$ is chosen.

In order to aid the choice of the appropriate standards, especially in relation to a large number of wavelengths for a complex unknown mixture, it is preferred to limit the choice to those defined by means of a minimal index. For the chosen standard the minimal index is at least the same as the differences between the absorptions of the unknown and the standards. Mathematically, this may be expressed as $i^2ab \leq i^2M$ where iM is the minimal index for the property, and iab is a measure of the deviation (called the proximity index) at all the chosen wavelengths between absorption of the unknown and a chosen standard b. That measure is defined by $$i(ab)^2 = \Sigma_i(D_{ia} - D_{ib})^2 \qquad (1)$$

where $D_{ia}$ is the optical density (or absorbence) of unknown a at wavelength i (or a derivative thereof e.g. a first, second or third derivative of that density), and $D_{ib}$ is the optical density (or absorbence) of standard b at that wavelength i (or a derivative thereof e.g. a first, second or third derivative of that density). The value of $D_1$ is the optical density or the optical density difference with respect to the baseline of the spectrum at that wavelength, or the baseline interpolated between 2 wavelengths on either side thereof.

If desired instead of the optical density $D_i$ a normalized density $W_i$ may be used where $W_i = D_i/\Sigma D_i$. This normalization avoids errors due to small electronic fluctuations in the apparatus and compensates for small differences in the optical path between the optical cells. In this case the proximity index is defined by $$i(ab)^2 = \Sigma(W_{ia} - W_{ib})^2 \qquad (2)$$

The indices can be weighted as desired for increasing resolution. One approach is to define the indices as follows.

$$I(ab)^m = \Sigma Abs\ Val(X_{ia} - X_{ib})^m/\sigma_i^n \qquad (3)$$

where $X_i$ is $D_i$ or $W_i$ or a mathematical combination thereof, $\sigma_i$ is the standard deviation for the set of samples considered (at that wavelength) and each of m and n, which is the same or different is the weighting factor which is positive but can be a whole number or a fraction. Other variants can be used with other weighting factors such as those involving the spectral experimental error $e_i$, where $e_i$ is the reproducibility of the spectral measurement at wavelength i. The choice between the different options for the weighted indices may be dictated by numerical efficiency.

The reproducibility of the experimental measurements in the standards may be at least 90% or 94% or 95%. The minimal index may be obtained for a reference standard samples set according to the following procedure, hereafter called the Minimal Index Procedure. The NIR spectra for 2 standard samples A and B and their property P e.g. density are determined. By means of equation (1), (2) or (3), the value of the proximity index $i_{ab}$ is determined via the absorptions at a series of wavelengths; this index is applicable to the difference in properties $P_a - P_b$ called $EP_{ab}$. This process is repeated with other pairs of standards c and d, e and f etc to obtain a series of Proximity Indices $i_{cd}$ etc with corresponding property differences $EP_{cd}$ etc. For different values of a parameter L which is greater than the indices $i_{ab}$ etc, the corresponding values of $EP_{ab}$ etc are averaged to give an average $EP_{ij}$ for that value of L; the different values of $EP_{ij} + t\sigma/\sqrt{K}$ are then plotted on a graph against L (the Proximity Index). $\sigma$ is the accuracy of the property determination and K is the number of pairs of samples for which $i_{ab}$ is inferior to a given L. t is the Student factor at a given level of confidence. The intercept is then measured between the curve obtained and a line usually horizontal which is the reproducibility of the property level at an appropriate confidence interval e.g. 90% or more usually 95%; The Abcissa position of the intercept gives the minimal index $i_{min}$, which is the minimum value of $i_{ab}$ for which Pa=Pb within the frame of experimental error.

From this minimal index by Procedure 1, the standards can be chosen which have values of $i^2_{ab} \leq i^2_{min}$ where in this case a is the unknown and b is a standard, as in this case the difference between Property a and Property b is less than or equal to $\sigma\sqrt{2}$, where $\sigma$ is the experimental error in measuring the property. Then from the property P values of the chosen standards, the property of the unknown is obtained by averaging those values, usually the arithmetic mean, but optionally with weighting.

The method of the invention may be used to determine more than one Property P at once, e.g. at least 2, such as 1-30 e.g. 2-10 properties at once. Each property of the standards has a particular unweighted Minimal Index, which may lie in the region $0-10^{-10}$ e.g. $10^{-2}$ to $10^{-8}$, in particular $5 \times 10^{-7}$ to $5 \times 10^{-4}$. If the Minimal Index chosen is the smallest for all the properties desired, then the same one may be used for all the properties and the standards chosen will be suitable for all the properties. The Minimal index for each property may be used separately, with different numbers of standards chosen for each property (assuming different Minimal Indices). If desired the same Minimal Index may be used, which is not the smallest, resulting in some of the chosen standards (with a higher Minimal Index) giving some properties of high accuracy and some with a lower Minimal Index giving some properties of less high accuracy.

The property to be determined may be of the sample being analyzed or a product obtained from that sample e.g. a product of blending the sample, as the property value obtained is derived from the standards, and they will have been determined as needed for the eventual use. Our EP304232 and 305090 referred to above describes such techniques when applied to use of NIR with correlation to blending or cracking operation; the same principles apply in the present method.

If the density of the standards in the data bank is sufficient to have $i^2ab \leq i^2min$ as is usually the case, the above procedure is very satisfactory. But there are occasions when the bank is incomplete, because of shortage of data of properties in a particular area i.e. a low density of standards or the sensitivity of the property to changes in absorption is so small, that a very small Minimal Index is required and there may be few standards with proximity indices meeting it. It is possible simply to choose a larger Minimal Index with e.g. 1-5 times such as 1.5-2 times the Minimal Index; the results may be less accurate than those from a smaller Minimal Index.

However, a more accurate approach with a low density of standards involves a special densification process of Procedure 2, in which random or semi random densification of the neighbourhood of the unknown is achieved by generation of synthetic standards, based on standards already in the bank. Each new synthetic standards may be obtained from combinations of standards taken at random from the bank but preferably it is obtained from the other standards by the constraint of choosing only a mixture of N standards for which $$(\text{Min})C_j - u_j \leq C_j \leq (\text{Max})C_j + u_j \quad (4)$$

and $$\Sigma C_{ij} = 1 \quad (5)$$

where $C_j$ is the fraction of component j in the sample $_i$.

Min $C_j$ is the minimum amount of $_j$ in the initial industrial calibration covering the correct area of $_j$ in the industrial mixture.

Max $C_j$ is the maximum amount of $_j$ in the initial industrial calibration covering the correct area of $_j$ in the industrial mixture.

uj is usually between 1 and 0.01 preferably between 0.5 and 0.1 and can be fixed for each property.

The constraints over the choice of such mixtures of N standards can also be equally fixed in the spectral area from which the samples will be drawn in order to remain in the areas of chemical nature.

The number of samples effectively drawn into the bank in this densification can be of several thousand generally 1000–2000. The calculation time is extended without significant deterioration in the results. If no further neighbours are found, the trawl of new samples drawn in is enlarged.

The spectrum of each mixture is calculated by the combination of the spectra of the standards used according to the formula $$S_{Mi} = \Sigma C_{ij} X S_j \quad (6)$$

where $S_j$ is the spectrum in the mixture of component $_j$ in the calibration matrix.

The properties of each mixture PMi can be calculated by a generally linear combination of the properties of the standards according to the formula $$P_{Mi} = \Sigma C_{ij} \times P_j \quad (7)$$

where $P_j$ is the property of component j.

In the case of non linear additive properties, appropriate mixing factors can be applied e.g. by blending factors or similar for density and viscosity.

Having obtained the spectrum and the properties of the synthetic mixtures, these can be used as "standards" to help determine the properties of an unknown sample in the same way as a conventional standard.

Instead of using either of the two above approaches, 1–7, a third type Procedure 3 may be used as follows. The Q nearest samples to unknown X can be found from a selection from the bank samples for which the proximity index to the unknown sample is (V) X $i_{min}$) where v is 0.1<v<10, (8) preferably 0.5<v<2 or $1 \leq v \leq 5$. Then by the method of least squares is found a generally linear combination of the standard products which are the Q nearest samples to reproduce the spectrum of X according to the equation.

$$S_x = \Sigma C_R \times S_r \quad (9)$$

where $C_r$ is the coefficient for sample R in the total Q and $S_R$ is the spectrum of sample R. The coefficient $C_R$ which can be normalized to $C_R=1$ or not and/or optimized by the least squares route, allows an estimation of the property $P_x$ according to the equation.

$$P_x = \Sigma C_R \times P_R \quad (10)$$

where $P_R$ is the property of sample R.

The eventual size of the estimation error can be derived by application of Gaussian theory, also called the propagation error (see Eq.10).

The above third approach can only be applied if the product X is situated inside the maximum extension of the standard products defined by equation (8). If this is not the case, X is outside the field of the actual bank of products and escapes from the area of knowledge of the method into the area of learning.

The densification process described in relation to equations 4–7, or 9 or 10 is usually applied to the method of the invention involving no correlation or regression techniques. However, if desired the densification process may be applied to increase the number of "standards" for consideration in an NIR analytical technique involving the correlation on regression techniques as described above e.g. MLR. The present invention also provides a method for adding an extra synthetic standard to a bank of known standards, each of which relates at least one absorption in the 600–2600 nm region (or derivative thereof) of a known material to a known property related to that material, wherein said property is of said material or is of a product or yield of a process from said material, which method comprises choosing from the bank at least 2 standards for which equations 4 and 5 above are met, considering mixing the chosen standards in at least one proportion to produce at least one mixture for use as a synthetic standard, and estimating the spectrum and property of said mixture according to equation 6 and 7 respectively and wherein said material X is a composition comprising part of a lubricating oil fraction obtainable from a vacuum distillation of oil.

The spectrum and property of each "mixture" can then be added to the bank and may be used to develop the models through known correlation/regression approach, e.g. as described in the above mentioned patents.

The method of the present invention is applicable to various petroleum hydrocarbon fractions, which comprise part (and only part) of a lubricating oil fraction e.g. from a vacuum distillation of oil after removal of materials boiling above 370° C. (under atmospheric pressure). Such fractions include the partly purified lube cut from the distillation, e.g. after at least one of the steps of dewaxing and dearomatizing and preferably both, (as in lube base oil) and the partly purified vacuum distillation residue e.g. after at least one of the steps of deasphalting, dewaxing and dearomatizing, and preferably all 3 (as in bright stock). Such fractions also include the aromatic extract of the lube oil cut or distillation residue, or a wax separated therefrom.

The method is preferably applied to lube base oils or bright stock. The base oil may be a 100–600 neutral or solvent or BS oil e.g. 100, 150, 200, 300, 400 or 500 neutral oil or BS solvent. It may have at least one of and preferably all of the following properties a density at 15° C. of 0.80–0.95 kg/l e.g. 0.85–0/92 kg/l, a kinematic viscosity at 40° C. of 10–1000 cSt e.g. 15–700 cSt, and at 100° C. of 0.5–50 cSt e.g. 1–40 cSt, a Flash Point of 180° C. min e.g. 190° C. min, a pour point of 0° C. maximum e.g. −5° C. or −7° C. maximum and a Viscosity Index of 80 min e.g. 90 min. The base oil may be present alone, or may be mixed with the aromatic extract as in process oils, which may have at least one of, and preferably all of the following properties, a density at 15° C. of 0.95–1.10 kg/l, e.g. 0.97–1.06 kg/l, a Kinematic Viscosity at 40° C. of at least 30 cSt e.g. at least 37 cSt, and at 100° C. of at most 50 cSt e.g. at most 45 cSt and a Flash Point of at least 185° C. e.g. 190° C. min. The base oil may also be present mixed with at least one wax e.g. in amount of, 0–50% such as 1–40% or 15–35% by weight as in "slack wax", the mixture of oil and solid wax separated in the dewaxing step, or waxes as in the residue from the dearomatization step.

The base oil may also be mixed with at least one non hydrocarbon additive to boost its effectiveness for lubricant use. Types of additives which may each be present in amounts of 0.01–10% by weight (based on the weight of base oil) e.g. 0.1–1% are (i) detergents/dispersants such as alkyl phenates and/or alkyl aryl sulphonates (ii) antioxidants such as phenol derivatives, (iii) viscosity index improvers and pour point depressants, such as alkyl poly(meth)acrylate homo and especially copolymers, styrene butadiene polymers and polyisobutylene (iv) anti corrosives, such as sulphur compounds, zinc sulphophosphates and dithiophosphates, and (v) solid or liquid lubricity additives, such as graphite, molybdenum disulphide and silicones.

The method may also be applied to the aromatic extract resulting from the extraction of aromatics (e.g. with furfural) from the lube cut of the vacuum distillate or the deasphalted vacuum residue. This aromatic extract is different from the base oil as it contains a much higher amount of aromatics, such as benzene, toluene and xylenes, and higher molecular weight aromatics e.g. of at least 30 carbons than the base oil. The aromatic extract may be used alone or mixed with an amount of base oil to form process oil.

The method may also be applied to solid or liquid paraffins or waxes e.g. as separated in a dewaxing step from the lube cut or the deasphalted residue. The wax may be mixed with base oil as in slack wax, or substantially free of base oil and may then if desired be further purified to produce a paraffin. Waxes may be used industrially while paraffins may be used for food and cosmetic uses.

The method is preferably applied for process control in a part of a refinery producing lubricants and by products therefrom, but may also be used for identification of unknowns e.g. for "finger printing" oils such as formulated oils.

Examples of properties that can be determined/estimated for the various materials are as follows. Where the material is a base oil (or formulated oil) the property may be at least one of the density, sulphur content, Flash Point, Flow Point, kinematic viscosity at 40° C. and at 100° C., Viscosity Index, aromatic carbon content, Polycyclic Aromatic hydrocarbon content, nitrogen base content, and inflammability according to Pensky Martens °C. When the material is a crude paraffin or slack wax, the property may be at least one of the density, viscosity e.g. at 40° C. or 100° C. and oil content. When the material is a process oil, the property may be at least one of the density, sulphur content, Polycyclic Aromatic hydrocarbon content, viscosity e.g. at 40° C. or 100° C. and the Flash Point e.g. Cleveland Flash Point.

In each of the above processes the property of a product determined or predicted by the method of the invention can be compared to the desired figure and notice taken of any deviations by adjusting the parameters of the process e.g. proportion or nature of feed and/or temperature/pressure etc to bring the property back to the desired figure. This control of the process, which may be a blending or separation process, is usually performed with a micro computer which is linked to the spectrometer and also performs the search for the standards $S_m$. The online control of the process is very efficient and very fast.

The present invention also provides an apparatus suitable for carrying out the method of the invention comprising an infra red spectrometer and a computer wherein the infra red spectrometer is linked to the computer program in such manner that the property may be determined continuously and in real time. The spectrometer is suitable for measuring spectra in the 600–2600 nm wavelength range and can be linked to a signal processing device to allow numerical treatment of the spectrum, preferably by Fourier transformation. The spectrometer receives at least one signal from a vessel containing product or from a feed or product line. The information obtained can be used as an information vector for the computer which is programmed to determine the property or yield eg via calculations on the proximity indices in relation to standards. Conveniently in relation to a process, the computer may be used in a closed loop feedback control system for controlling processing equipment eg changing the process parameters in response to variations in the property and/or yield of product from the desired value, measurement of more than one absorption in the NIR spectrum of the product and/or feed.

The benefits of invention allow improvements in modelling with the following areas, identification and classification of novel products, simultaneous estimation of all of P properties on a sample without the need for generating P different models, and with the option of automatic upgrading of the model, the method being self learning or adjusting. The method of the invention overcomes the difficulties with the classical regressional approach, in particular avoiding all difficulties with numerical stability of the models, allowing easy and rapid identification and classification of a sample of a product analyzed by spectral recognition and then instant conclusions as to whether the sample is known or unknown, allowing simultaneous determination of many properties and whether the property is simply additive or synergetic in relation to a blend composition; the latter is particularly useful for different blend indices and the indices considered.

The method also allows an extension of the field of application of the method without the need to rewrite the model, apart from the need to integrate the new samples which are inside or outside the previous field of validity of the method. This possibility of automatic learning, which is not possessed by traditional regression techniques, is a decisive advantage in the framework of continuous inline industrial control processes, because it allows the return of the industrial plant operations to the model in a certain and rapid manner in a minimum time and with all the properties considered in the model. In contrast classical regression methods would necessitate the redevelopment of all the models, which is long and laborious without being able to guarantee the result of the new model obtained, because a new validation period is necessary; in addition during the redevelopment of the model any commercial refinery use of the model is very limited. Furthermore, the method of invention allows equally the easy extension to a number of properties, which are simply incorporated into the known bank.

This remarkable possibility is true not only for conventional properties such as physical chemical and/or rheological properties, but also for complex ones. The methods of the invention equally allow application of the models from one apparatus to another and from one spectral region to another, where conventional regressive method cannot give satisfactory solutions. This apparatus portability is made possible by the fact that the differences between different spectra are the same in one apparatus as another, for the same type of spectrometer being considered (e.g. network scatter, Fourier transform, accousto optical system AOTS, diode array etc). This portability between spectral regions depends on the fact that as the spectral regions are intercorrelated, the relations between the spectra are maintained between one another.

The invention is illustrated in the following Examples in which the Minimal Index is calculated according to the Minimal index Procedure described above. Mathematically the steps concerned are as follows.

For each couple of standard samples i, j, the Proximity Index $i_{ij}$ is determined from the NIR spectra by use of equation 1, 2, or 3 and the properties are measured. For each Proximity index is calculated the absolute difference $EP_{ij}$ between the properties of the samples. The Minimal Index for property P is obtained from the average $EM_p(L)$ of $EP_{ij}$ for different values of L when $L \geq ij$. Thus the $EM_p(L)=1/K \Sigma\Sigma EP_{ij}$ for each of K samples for which $ij \leq L$.

EMpL+tσ(M) is plotted against the proximity index and in addition there is plotted the reproducibility of the standard, method at a given level of confidence as defined in the Minimal Index Procedure above. The intercept of the curve from EMpL and the reproducibility give the upper limit i.e. the Minimal Index.

For the Examples the data is expressed in Tables in a form as shown below in which the data is as follows.

| Proximity Index | | | Absorption | | |
|---|---|---|---|---|---|
| Wavelength λ | | Un- | | Stan- | Stan- |
| cm$^{-1}$ | nm | Weighting | known | Estimated | dard A | dard B |
| Property l | | | | | | |
| Property j | | | | | | |
| Property m | | | | | | |

The wavelengths chosen are shown in columns 1 and 2.

Column 3 gives the weight loading associated with each wavelength for the proximity index for the standards; 1 denotes no loading.

Column 4 shows for the unknown sample the absorption at the various wavelengths and at the bottom the properties of that sample determined by standard methods.

Column 5 shows for the unknown sample the estimated values of the properties and the absorptions using the method of the invention based on the properties and absorptions of the chosen standards.

Columns 6, 7 etc show the values of the absorptions and properties for the standards chosen from the bank.

Line 2 give the value of the proximity index between the unknown sample and each of the chosen standards.

EXAMPLES 1

Determination of the Properties of a Base Oil

The NIR spectrum of a base oil D which was a 500 neutral oil was measured between 4800 and 4000 cm$^{-1}$ with normalisation of the absorbances, [the base line being taken at 4780 cm$^{-1}$]. NIR spectra were recorded for a series of standard base oils of known properties. By the Minimal Index Procedure described above, with use of Equation 2, and non weighting of the absorbancies, the Minimal Index was calculated to be $5 \times 10^{-7}$. Following reference to the bank of data on the standard base oils, 3 standards 1A, 1B and 1C were found with the proximity index with respect to oil D less than $5 \times 10^{-7}$. The properties of those standards and their spectra are shown in Table 1.1. By averaging the properties of the standard samples, various properties were obtained for the oil D. The Table 1 shows the estimated properties as well as measured properties of oil D for comparison.

All the properties were determined in a single analysis and without any regressional type calculations and with a degree of precision in line with the reproducibility of the reference methods.

Other properties of D can be determined in a similar way.

EXAMPLE 2

Determination of the Properties of a Process Oil

The method of Example 1 was repeated with a process Oil Reference 2D of "Enerthene" type which was a mixture of neutral base oil and aromatic-containing vacuum distillate extract. From a bank of standard process oils of this type, the band of the sphere of identity was found to be $5 \times 10^{-7}$, by the Minimal Index Procedure. 3 standard oils 2A, 2B and 2C were found with proximity indices with respect to 2D less than the Minimal index. The properties of oils 2A, 2B, 2C and their spectra and the spectrum of 2D are given in Table 2.1. By arithmetic mean averaging of the properties of 2A, 2B and 2C, the properties of 2D were estimated, and these together with the measured properties of 2D are given also in Table 2.1.

The single analysis gave all the properties without regression calculation and with an accuracy in line with the reproducibility of the reference methods. Other properties can be determined in a similar way.

In Table 2.1, the expression 4.20 E-04 means $4.2 \times 10^{-4}$ and PCA means Polycyclic Aromatic hydrocarbon.

EXAMPLE 3

Determination of the Properties of a Crude Paraffin

The method of Example 1 was repeated with a crude paraffin (a "slack" wax), which was a mixture of paraffin wax and base oil called Gatsche D. From a bank of standard crude paraffins and their properties and spectra, the Minimal Index was found to be $5 \times 10^{-5}$, by the Minimal Index Procedure. 3 standard crude paraffins Gatsche 3A, 3B and 3C were found with proximity indices with respect to 3D inside the sphere of identity. The properties of paraffins 3A, 3B, 3C and their spectra, and the spectrum of 3D are given in Table 3.1. By arithmetic means averaging of the properties of 3A, 3B and 3C the properties of 3D were estimated, and these together with the measured properties of 3D are given also in Table 3.1. The properties determined were density, viscosity at 100° C. and oil content. The determination of the oil content of crude paraffin according to the above procedure is particularly remarkable because no on line process capable of measuring this is known today.

All the properties were determined in a single analysis without any regression type calculation and with an accuracy in line with the reproducibility of the reference methods. Other properties of D can be determined in a similar way.

TABLE 1.1

Determination of the properties of Base Oil

| Proximity Index Wavelength | | | Oil D | Oil D | Oil 1A | Oil 1B | Oil 1C |
|---|---|---|---|---|---|---|---|
| λ(cm-1) | λ(nm) | Loading | Measured | Estimated | $8.8 \times 10^{-8}$ | $4 \times 10^{-8}$ | $4.6 \times 10^{-7}$ |
| 4632 | 2158 | 1 | 4,9000000E-04 | 5,0333333E-04 | 5,1000000E-04 | 5,0000000E-04 | 5,0000000E-04 |
| 4624 | 2162 | 1 | 5,7000000E-04 | 5,8000000E-04 | 5,9000000E-04 | 5,9000000E-04 | 5,6000000E-04 |
| 4616 | 2166 | 1 | 6,1000000E-04 | 6,2000000E-04 | 6,3000000E-04 | 6,1000000E-04 | 6,2000000E-04 |
| 4600 | 2173 | 1 | 7,8000000E-04 | 7,7000000E-04 | 7,8000000E-04 | 7,6000000E-04 | 7,7000000E-04 |
| 4592 | 2177 | 1 | 8,4000000E-04 | 8,4000000E-04 | 8,5000000E-04 | 8,3000000E-04 | 8,4000000E-04 |
| 4576 | 2185 | 1 | 8,5000000E-04 | 8,4666667E-04 | 8,4000000E-04 | 8,5000000E-04 | 8,5000000E-04 |
| 4568 | 2189 | 1 | 8,1000000E-04 | 8,0333333E-04 | 8,0000000E-04 | 8,1000000E-04 | 8,0000000E-04 |
| 4560 | 2192 | 1 | 8,6000000E-04 | 8,7333333E-04 | 8,8000000E-04 | 8,8000000E-04 | 8,6000000E-04 |
| 4540 | 2202 | 1 | 9,3000000E-04 | 9,2333333E-04 | 9,2000000E-04 | 9,2000000E-04 | 9,3000000E-04 |
| 4504 | 2220 | 1 | 1,2800000E-03 | 1,2933333E-03 | 1,2900000E-03 | 1,3000000E-03 | 1,2900000E-03 |
| 4472 | 2236 | 1 | 1,9900000E-03 | 2,0000000E-03 | 2,0000000E-03 | 2,0000000E-03 | 2,0000000E-03 |
| 4440 | 2252 | 1 | 4,2300000E-03 | 4,2433333E-03 | 4,2500000E-03 | 4,2500000E-03 | 4,2300000E-03 |
| 4432 | 2256 | 1 | 5,5300000E-03 | 5,5233333E-03 | 5,5300000E-03 | 5,5500000E-03 | 5,4900000E-03 |
| 4424 | 2260 | 1 | 7,4300000E-03 | 7,4266667E-03 | 7,4300000E-03 | 7,4500000E-03 | 7,4000000E-03 |
| 4416 | 2264 | 1 | 9,7800000E-03 | 9,7900000E-03 | 9,8000000E-03 | 9,8200000E-03 | 9,7500000E-03 |
| 4408 | 2268 | 1 | 1,2690000E-02 | 1,2693333E-02 | 1,2710000E-02 | 1,2730000E-02 | 1,2640000E-02 |
| 4400 | 2272 | 1 | 1,5840000E-02 | 1,5810000E-02 | 1,5810000E-02 | 1,5870000E-02 | 1,5750000E-02 |
| 4392 | 2276 | 1 | 1,7970000E-02 | 1,7940000E-02 | 1,7960000E-02 | 1,7970000E-02 | 1,7890000E-02 |
| 4382 | 2282 | 1 | 1,9140000E-02 | 1,9126667E-02 | 1,9150000E-02 | 1,9140000E-02 | 1,9090000E-02 |
| 4376 | 2285 | 1 | 1,9700000E-02 | 1,9696667E-02 | 1,9730000E-02 | 1,9720000E-02 | 1,9640000E-02 |
| 4368 | 2289 | 1 | 2,0450000E-02 | 2,0460000E-02 | 2,0480000E-02 | 2,0460000E-02 | 2,0440000E-02 |
| 4352 | 2297 | 1 | 2,6140000E-02 | 2,6106667E-02 | 2,6130000E-02 | 2,6130000E-02 | 2,6060000E-02 |
| 4344 | 2302 | 1 | 3,2330000E-02 | 3,2136667E-02 | 3,2300000E-02 | 3,2330000E-02 | 3,2320000E-02 |
| 4330 | 2309 | 1 | 4,3200000E-02 | 4,3226667E-02 | 4,3290000E-02 | 4,3170000E-02 | 4,3220000E-02 |
| 4320 | 2314 | 1 | 3,6600000E-02 | 3,6566667E-02 | 3,6550000E-02 | 3,6550000E-02 | 3,6600000E-02 |
| 4312 | 2319 | 1 | 2,9970000E-02 | 2,9933333E-02 | 2,9930000E-02 | 2,9970000E-02 | 2,9900000E-02 |
| 4304 | 2323 | 1 | 2,6610000E-02 | 2,6566667E-02 | 2,6570000E-02 | 2,6590000E-02 | 2,6540000E-02 |
| 4296 | 2327 | 1 | 2,4540000E-02 | 2,4500000E-02 | 2,4490000E-02 | 2,4510000E-02 | 2,4500000E-02 |
| 4290 | 2331 | 1 | 2,3810000E-02 | 2,3830000E-02 | 2,3820000E-02 | 2,3870000E-02 | 2,3800000E-02 |
| 4280 | 2336 | 1 | 2,5390000E-02 | 2,5346667E-02 | 2,5360000E-02 | 2,5340000E-02 | 2,5340000E-02 |
| 4272 | 2340 | 1 | 2,9140000E-02 | 2,9163333E-02 | 2,9190000E-02 | 2,9140000E-02 | 2,9160000E-02 |
| 4258 | 2348 | 1 | 3,7380000E-02 | 3,7363333E-02 | 3,7330000E-02 | 3,7370000E-02 | 3,7390000E-02 |
| 4248 | 2354 | 1 | 3,2840000E-02 | 3,2830000E-02 | 3,2820000E-02 | 3,2820000E-02 | 3,2850000E-02 |
| 4240 | 2358 | 1 | 2,8100000E-02 | 3,8090000E-02 | 2,8080000E-02 | 2,8100000E-02 | 2,8090000E-02 |
| 4232 | 2362 | 1 | 2,6100000E-02 | 2,6083333E-02 | 2,6120000E-02 | 2,6050000E-02 | 2,6080000E-02 |
| 4224 | 2367 | 1 | 2,5820000E-02 | 2,5850000E-02 | 2,5830000E-02 | 2,5840000E-02 | 2,5880000E-02 |
| 4212 | 2374 | 1 | 2,5640000E-02 | 2,5653333E-02 | 2,5670000E-02 | 2,5620000E-02 | 2,5670000E-02 |
| 4200 | 2380 | 1 | 2,5860000E-02 | 2,5853333E-02 | 2,5820000E-02 | 2,5840000E-02 | 2,5900000E-02 |

| Proximity Index | | | Oil D | Oil D | Oil 1A | Oil 1B | Oil 1C |
|---|---|---|---|---|---|---|---|
| λ(cm-1) | λ(nm) | Loading | Measured | Estimated | $8.8 \times 10^{-8}$ | $4 \times 10^{-8}$ | $4.6 \times 10^{-7}$ |
| 4192 | 2385 | 1 | 2,5820000E-02 | 2,5846667E-02 | 2,5820000E-02 | 2,5800000E-02 | 2,5920000E-02 |
| 4184 | 2390 | 1 | 2,5970000E-02 | 2,6003333E-02 | 2,6010000E-02 | 2,5970000E-02 | 2,6030000E-02 |
| 4176 | 2394 | 1 | 2,6210000E-02 | 2,6236667E-02 | 2,6240000E-02 | 2,6190000E-02 | 2,6280000E-02 |
| 4170 | 2398 | 1 | 2,6600000E-02 | 2,6593333E-02 | 2,6560000E-02 | 2,6580000E-02 | 2,6640000E-02 |
| 4160 | 2403 | 1 | 2,6370000E-02 | 2,6390000E-02 | 2,6380000E-02 | 2,6370000E-02 | 2,6420000E-02 |
| 4152 | 2408 | 1 | 2,5710000E-02 | 2,5710000E-02 | 2,5690000E-02 | 2,5710000E-02 | 2,5730000E-02 |
| 4136 | 2417 | 1 | 2,4620000E-02 | 2,4633333E-02 | 2,4600000E-02 | 2,4640000E-02 | 2,4660000E-02 |
| 4120 | 2427 | 1 | 2,3990000E-02 | 2,3993333E-02 | 2,3980000E 02 | 2,4000000E-02 | 2,4000000E-02 |
| 4104 | 2436 | 1 | 2,3060000E-02 | 1,5370000E-02 | 2,3050000E-02 | 2,3060000E-02 | 2,3090000E-02 |
| 4092 | 2443 | 1 | 2,2600000E-02 | 2,2613333E-02 | 2,2600000E-02 | 2,2610000E-02 | 2,2630000E-02 |
| 4080 | 2450 | 1 | 2,2730000E-02 | 2,2740000E-02 | 2,2720000E-02 | 2,2730000E-02 | 2,2770000E-02 |
| 4072 | 2455 | 1 | 2,3350000E-02 | 2,3363333E-02 | 2,3330000E-02 | 2,3370000E-02 | 2,3390000E-02 |
| 4068 | 2458 | 1 | 2,3640000E-02 | 2,3636667E-02 | 2,3650000E-02 | 2,3610000E-02 | 2,3650000E-02 |
| 4048 | 2470 | 1 | 2,0700000E-02 | 2,0726667E-02 | 2,0720000E-02 | 2,0720000E-02 | 2,0740000E-02 |
| 4000 | 2500 | 1 | 1,5150000E-02 | 1,5166667E-02 | 1,5170000E-02 | 1,5140000E-02 | 1,5190000E-02 |
| Density kg/l | | | 0,8901 | 0,8898 | 0,8900 | 0,8898 | 0,8896 |
| Sulphur % | | | 1,1 | 1,11 | 1,1 | 1,12 | 1,12 |
| Pour Point °C. | | | −9 | −9 | −10 | −9 | −8 |
| Viscosity at 40° C. cSt | | | 96,8 | 97,04 | 94,08 | 98,3 | 98,74 |
| Viscosity at 100° C. cSt | | | 10,84 | 10,85 | 10,65 | 10,92 | 11 |
| Viscosity Index VI | | | 95 | 95,2 | 95,5 | 94,7 | 95,5 |
| Aromatic Carbon % | | | 8 | 7,6 | 7,5 | 7,4 | 8 |
| Inflammability Pensky-Martens °C. | | | 239 | 241 | 244 | 239 | 240 |

TABLE 1.1-continued

Determination of the properties of Base Oil

| | | | | | |
|---|---|---|---|---|---|
| Nitrogen base content ppm | 60 | 59 | 56 | 60 | 63 |

TABLE 2.1

Determination of the properties of a process oil

| Proximity Index Wavelength | | | Oil D | Oil D Estimated | Oil 2A | Oil 2B | Oil 2C |
|---|---|---|---|---|---|---|---|
| $\lambda$(cm-1) | $\lambda$(nm) | Loading | Measured | $1.09 \times 10^{-7}$ | $3.5 \times 10^{-7}$ | $1.19 \times 10^{-7}$ | $2.19 \times 10^{-7}$ |
| 4700 | 2127 | 1 | 4,2000000E-04 | 3,5000000E-04 | 3,2000000E-04 | 3,5000000E-04 | 3,8000000E-04 |
| 4688 | 2133 | 1 | 7,3000000E-04 | 6,4666667E-04 | 6,1000000E-04 | 6,7000000E-04 | 6,6000000E-04 |
| 4680 | 2136 | 1 | 9,8000000E-04 | 9,6333333E-04 | 9,6000000E-04 | 9,4000000E-04 | 9,9000000E-04 |
| 4664 | 2144 | 1 | 1,8300000E-03 | 1,7833333E-03 | 1,7600000E-03 | 1,7600000E-03 | 1,8300000E-03 |
| 4656 | 2147 | 1 | 2,1600000E-03 | 2,0900000E-03 | 2,0900000E-03 | 2,0600000E-03 | 2,1200000E-03 |
| 4648 | 2151 | 1 | 2,5100000E-03 | 2,4300000E-03 | 2,4100000E-03 | 2,4100000E-03 | 2,4700000E-03 |
| 4632 | 2158 | 1 | 2,9500000E-03 | 2,9233333E-03 | 2,8600000E-03 | 2,9100000E-03 | 3,0000000E-03 |
| 4624 | 2162 | 1 | 3,1100000E-03 | 3,0966667E-03 | 3,0100000E-03 | 3,0800000E-03 | 3,2000000E-03 |
| 4616 | 2166 | 1 | 3,1700000E-03 | 3,1833333E-03 | 3,1200000E-03 | 3,1800000E-03 | 3,2500000E-03 |
| 4600 | 2173 | 1 | 3,1000000E-03 | 3,1466667E-03 | 3,1100000E-03 | 3,1600000E-03 | 3,1700000E-03 |
| 4592 | 2177 | 1 | 3,0700000E-03 | 3,0500000E-03 | 3,0000000E-03 | 3,0500000E-03 | 3,1000000E-03 |
| 4576 | 2185 | 1 | 2,6300000E-03 | 2,5800000E-03 | 2,5500000E-03 | 2,5800000E-03 | 2,6100000E-03 |
| 4568 | 2189 | 1 | 2,3200000E-03 | 2,3133333E-03 | 2,2500000E-03 | 2,3100000E-03 | 2,3800000E-03 |
| 4560 | 2192 | 1 | 2,2300000E-03 | 2,1933333E-03 | 2,1500000E-03 | 2,1600000E-03 | 2,2700000E-03 |
| 4540 | 2202 | 1 | 2,0200000E-03 | 1,9966667E-03 | 2,0000000E-03 | 1,9800000E-03 | 2,0100000E-03 |
| 4504 | 2220 | 1 | 2,3400000E-03 | 2,3133333E-03 | 2,2900000E-03 | 2,2900000E-03 | 2,3600000E-03 |
| 4472 | 2236 | 1 | 3,2300000E-03 | 3,2000000E-03 | 3,1500000E-03 | 3,1900000E-03 | 3,2600000E-03 |
| 4440 | 2252 | 1 | 6,1400000E-03 | 6,0966667E-03 | 6,0800000E-03 | 6,0600000E-03 | 6,1500000E-03 |
| 4432 | 2256 | 1 | 7,8000000E-03 | 7,8100000E-03 | 7,7800000E-03 | 7,7700000E-03 | 7,8800000E-03 |
| 4424 | 2260 | 1 | 1,0270000E-02 | 1,0210000E-02 | 1,0180000E-02 | 1,0190000E-02 | 1,0260000E-02 |
| 4416 | 2264 | 1 | 1,3160000E-02 | 1,3130000E-02 | 1,3100000E-02 | 1,3090000E-02 | 1,3200000E-02 |
| 4408 | 2268 | 1 | 1,6510000E-02 | 1,6490000E-02 | 1,6430000E-02 | 1,6470000E-02 | 1,6570000E-02 |
| 4400 | 2272 | 1 | 1,9410000E-02 | 1,9386667E-02 | 1,9340000E-02 | 1,9350000E-02 | 1,9470000E-02 |
| 4392 | 2276 | 1 | 2,0970000E-02 | 2,0963333E-02 | 2,0930000E-02 | 2,0940000E-02 | 2,1020000E-02 |
| 4382 | 2282 | 1 | 2,1900000E-02 | 2,1913333E-02 | 2,1870000E-02 | 2,1930000E-02 | 2,1940000E-02 |
| 4376 | 2285 | 1 | 2,2570000E-02 | 2,2530000E-02 | 2,2510000E-02 | 2,2520000E-02 | 2,2560000E-02 |
| 4368 | 2289 | 1 | 2,3080000E-02 | 2,3053333E-02 | 2,3030000E-02 | 2,3030000E-02 | 2,3100000E-02 |
| 4352 | 2297 | 1 | 2,8240000E-02 | 2,8183333E-02 | 2,8170000E-02 | 2,8160000E-02 | 2,8220000E-02 |
| 4344 | 2302 | 1 | 3,3140000E-02 | 3,3196667E-02 | 3,3230000E-02 | 3,3220000E-02 | 3,3140000E-02 |
| 4330 | 2309 | 1 | 3,8690000E-02 | 3,8780000E-02 | 3,8850000E-02 | 3,8810000E-02 | 3,8680000E-02 |
| 4320 | 2314 | 1 | 3,4290000E-02 | 3,4320000E-02 | 3,4360000E-02 | 3,4300000E-02 | 3,4300000E-02 |
| 4312 | 2319 | 1 | 2,0890000E-02 | 3,0883333E-02 | 3,0830000E-02 | 3,0870000E-02 | 3,0950000E-02 |
| 4304 | 2323 | 1 | 2,8580000E-02 | 2,8576667E-02 | 2,8560000E-02 | 2,8560000E-02 | 2,8610000E-02 |
| 4296 | 2327 | 1 | 2,6340000E-02 | 2,6386667E-02 | 2,6340000E-02 | 2,6400000E-02 | 2,6420000E-02 |
| 4290 | 2331 | 1 | 2,5250000E-02 | 2,5223333E-02 | 2,5200000E-02 | 2,5230000E-02 | 2,5240000E-02 |
| 4280 | 2336 | 1 | 2,5780000E-02 | 2,5786667E-02 | 2,5800000E-02 | 2,5780000E-02 | 2,5780000E-02 |
| 4272 | 2340 | 1 | 2,8200000E-02 | 2,8263333E-02 | 2,8300000E-02 | 2,8290000E-02 | 2,8200000E-02 |
| 4258 | 2348 | 1 | 3,2280000E-02 | 3,2410000E-02 | 3,2500000E-02 | 3,2470000E-02 | 3,2260000E-02 |
| 4248 | 2354 | 1 | 3,9760000E-02 | 2,9810000E-02 | 2,9870000E-02 | 2,9820000E-02 | 2,9740000E-02 |
| 4240 | 2358 | 1 | 2,7120000E-02 | 2,7133333E-02 | 2,7120000E-02 | 2,7170000E-02 | 2,7110000E-02 |
| 4232 | 2362 | 1 | 2,5410000E-02 | 2,5393333E-02 | 2,5410000E-02 | 2,5410000E-02 | 2,5360000E-02 |
| 4224 | 2367 | 1 | 2,3930000E-02 | 2,4000000E-02 | 2,4000000E-02 | 2,4020000E-02 | 2,3980000E-02 |

| Proximity Index | | | | Oil D Estimated | Oil 2A | Oil 2B | Oil 2C |
|---|---|---|---|---|---|---|---|
| $\lambda$(cm-1) | $\lambda$(nm) | Loading | Measured | $1.09 \times 10^{-7}$ | $3.5 \times 10^{-7}$ | $1.19 \times 10^{-7}$ | $2.19 \times 10^{-7}$ |
| 4212 | 2374 | 1 | 2,2630000E-02 | 2,2630000E-02 | 2,2680000E-02 | 2,2650000E-02 | 2,2560000E-02 |
| 4200 | 2380 | 1 | 2,2060000E-02 | 2,2106667E-02 | 2,2140000E-02 | 2,2160000E-02 | 2,2020000E-02 |
| 4192 | 2385 | 1 | 2,2010000E-02 | 2,2043333E-02 | 2,2110000E-02 | 2,2070000E-02 | 2,1950000E-02 |
| 4184 | 2390 | 1 | 2,2220000E-02 | 2,2226667E-02 | 2,2310000E-02 | 2,2230000E-02 | 2,2140000E-02 |
| 4176 | 2394 | 1 | 2,2780000E-02 | 2,2816667E-02 | 2,2860000E-02 | 2,2840000E-02 | 2,2750000E-02 |
| 4170 | 2398 | 1 | 2,3160000E-02 | 2,3213333E-02 | 2,3290000E-02 | 2,3210000E-02 | 2,3140000E-02 |
| 4160 | 2403 | 1 | 2,2840000E-02 | 2,2850000E-02 | 2,2890000E-02 | 2,2860000E-02 | 2,2800000E-02 |
| 4152 | 2408 | 1 | 2,1810000E-02 | 2,1843333E-02 | 2,1900000E-02 | 2,1860000E-02 | 2,1770000E-02 |
| 4136 | 2417 | 1 | 2,0630000E-02 | 2,0630000E-02 | 2,0700000E-02 | 2,0640000E-02 | 2,0550000E-02 |
| 4120 | 2427 | 1 | 2,0170000E-02 | 2,0186667E-02 | 2,0240000E-02 | 2,0220000E-02 | 2,0100000E-02 |
| 4104 | 2436 | 1 | 1,9520000E-02 | 1,9563333E-02 | 1,9590000E-02 | 1,9590000E-02 | 1,9510000E-02 |
| 4092 | 2443 | 1 | 1,9530000E-02 | 1,9593333E-02 | 1,9640000E-02 | 1,9610000E-02 | 1,9530000E-02 |
| 4080 | 2450 | 1 | 2,1540000E-02 | 2,1513333E-02 | 2,1550000E-02 | 2,1530000E-02 | 2,1460000E-02 |
| 4072 | 2455 | 1 | 2,3530000E-02 | 2,3530000E-02 | 2,3550000E-02 | 2,3530000E-02 | 2,3510000E-02 |

TABLE 2.1-continued

Determination of the properties of a process oil

| | | | | | | | |
|---|---|---|---|---|---|---|---|
| 4068 | 2458 | 1 | 2,3430000E-02 | 2,3443333E-02 | 2,3460000E-02 | 2,3450000E-02 | 2,3420000E-02 |
| 4048 | 2470 | 1 | 1,8990000E-02 | 1,9010000E-02 | 2,9050000E-02 | 1,9020000E-02 | 1,8960000E-02 |
| 4000 | 2500 | 1 | 1,4630000E-02 | 1,4593333E-02 | 1,4620000E-02 | 1,4580000E-02 | 1,4580000E-02 |
| Density kg/l | | | 0,9348 | 0,9351 | 0,9350 | 0,9345 | 0,9360 |
| Sulphur % | | | 2,25 | 2,28 | 2,37 | 1,98 | 2,51 |
| PCA % | | | 2,60 | 2,57 | 2,88 | 2,74 | 2,1 |
| Viscosity at 100° C. sCt | | | 33,19 | 33,22 | 33,23 | 32,25 | 34,18 |
| Flash Point Cleveland °C. | | | 310 | 311 | 310 | 308 | 315 |

TABLE 3.1

Determination of the properties of a crude paraffin

| Proximity Index Wavelength | | | Gatsche D | Gatsche D | Gatsche 3A | Gatsche 3B | Gatsche 3C |
|---|---|---|---|---|---|---|---|
| $\lambda$(cm-1) | $\lambda$(nm) | Loading | Measured | Estimated | $6.76 \times 10^{-6}$ | $4.6 \times 10^{-6}$ | $2.69 \times 10^{-6}$ |
| 4680 | 2136 | 1 | 7,0000000E-05 | 8,0000000E-05 | 8,0000000E-05 | 8,0000000E-05 | 8,0000000E-05 |
| 4664 | 2144 | 1 | 1,9000000E-04 | 1,4666667E-04 | 1,2000000E-04 | 2,0000000E-04 | 1,2000000E-04 |
| 4656 | 2147 | 1 | 3,0000000E-04 | 7,6666667E-05 | 1,0000000E-04 | 6,0000000E-05 | 7,0000000E-05 |
| 4648 | 2151 | 1 | 2,7000000E-04 | 1,6333333E-04 | 1,9000000E-04 | 1,4000000E-04 | 1,6000000E-04 |
| 4624 | 2162 | 1 | 1,9000000E-04 | 3,0333333E-04 | 4,1000000E-04 | 2,4000000E-04 | 2,6000000E-04 |
| 4616 | 2166 | 1 | 4,3000000E-04 | 2,0333333E-04 | 4,1000000E-04 | 1,0000000E-04 | 1,0000000E-04 |
| 4600 | 2173 | 1 | 4,9000000E-04 | 3,4333333E-04 | 3,6000000E-04 | 3,0000000E-04 | 3,7000000E-04 |
| 4592 | 2177 | 1 | 5,3000000E-04 | 3,9333333E-04 | 3,8000000E-04 | 4,0000000E-04 | 4,0000000E-04 |
| 4576 | 2185 | 1 | 7,7000000E-04 | 3,0000000E-04 | 3,0000000E-04 | 2,9000000E-04 | 3,1000000E-04 |
| 4568 | 2189 | 1 | 8,1000000E-04 | 3,5333333E-04 | 5,5000000E-04 | 2,5000000E-04 | 2,6000000E-04 |
| 4560 | 2192 | 1 | 4,9000000E-04 | 4,1000000E-04 | 6,4000000E-04 | 2,9000000E-04 | 3,0000000E-04 |
| 4540 | 2202 | 1 | 6,1000000E-04 | 4,9666667E-04 | 4,7000000E-04 | 5,2000000E-04 | 5,0000000E-04 |
| 4504 | 2220 | 1 | 8,9000000E-04 | 7,3666667E-04 | 7,9000000E-04 | 7,2000000E-04 | 7,0000000E-04 |
| 4472 | 2236 | 1 | 1,3800000E-03 | 1,2533333E-03 | 1,3500000E-03 | 1,2100000E-03 | 1,2000000E-03 |
| 4440 | 2252 | 1 | 3,2900000E-03 | 3,0766667E-03 | 3,1900000E-03 | 3,0400000E-03 | 3,0000000E-03 |
| 4432 | 2256 | 1 | 4,0600000E-03 | 4,1500000E-03 | 4,1900000E-03 | 4,1400000E-03 | 4,1200000E-03 |
| 4424 | 2260 | 1 | 5,5800000E-03 | 5,4933333E-03 | 5,5500000E-03 | 5,5500000E-03 | 5,3800000E-03 |
| 4416 | 2264 | 1 | 7,3800000E-03 | 7,4700000E-03 | 7,3900000E-03 | 7,6000000E-03 | 7,4200000E-03 |
| 4408 | 2268 | 1 | 9,9510000E-03 | 9,9533333E-03 | 9,8500000E-03 | 1,0010000E-02 | 1,0000000E-02 |
| 4400 | 2272 | 1 | 1,2390000E-02 | 1,2430000E-02 | 1,2420000E-02 | 1,2440000E-02 | 1,2430000E-02 |
| 4392 | 2276 | 1 | 1,3630000E-02 | 1,3890000E-02 | 1,3740000E-02 | 1,3900000E-02 | 1,4030000E-02 |
| 4382 | 2282 | 1 | 1,5770000E-02 | 1,5903333E-02 | 1,5730000E-02 | 1,6050000E-02 | 1,5930000E-02 |
| 4376 | 2285 | 1 | 1,7070000E-02 | 1,7346667E-02 | 1,7260000E-02 | 1,7520000E-02 | 1,7260000E-02 |
| 4368 | 2289 | 1 | 1,8580000E-02 | 1,6422000E-02 | 1,1856000E-02 | 1,8760000E-02 | 1,8650000E-02 |
| 4352 | 2297 | 1 | 2,7390000E-02 | 2,7546667E-02 | 2,7510000E-02 | 2,7420000E-02 | 2,7710000E-02 |
| 4344 | 2302 | 1 | 3,6750000E-02 | 3,7120000E-02 | 3,7070000E-02 | 3,7120000E-02 | 3,7170000E-02 |
| 4330 | 2309 | 1 | 4,8280000E-02 | 4,8853333E-02 | 4,8950000E-02 | 4,8810000E-02 | 4,8800000E-02 |
| 4320 | 2314 | 1 | 3,3850000E-02 | 3,4233333E-02 | 3,3910000E-02 | 3,4130000E-02 | 3,4600000E-02 |
| 4312 | 2319 | 1 | 2,5770000E-02 | 2,5913333E-02 | 2,5860000E-02 | 2,5900000E-02 | 2,5980000E-02 |
| 4304 | 2323 | 1 | 2,2440000E-02 | 2,2740000E-02 | 2,2410000E-02 | 2,2710000E-02 | 2,3100000E-02 |
| 4296 | 2327 | 1 | 2,1050000E-02 | 2,1210000E-02 | 2,1110000E-02 | 2,1260000E-02 | 2,1260000E-02 |
| 4290 | 2331 | 1 | 2,1120000E-02 | 2,1233333E-02 | 2,1130000E-02 | 2,1260000E-02 | 2,1310000E-02 |
| 4280 | 2336 | 1 | 2,4680000E-02 | 2,4666667E-02 | 2,4510000E-02 | 2,4760000E-02 | 2,4730000E-02 |
| 4272 | 2340 | 1 | 3,1630000E-02 | 3,1763333E-02 | 3,1700000E-02 | 3,1840000E-02 | 3,1750000E-02 |
| 4258 | 2348 | 1 | 4,5820000E-02 | 4,6073333E-02 | 4,6130000E-02 | 4,6110000E-02 | 4,5980000E-02 |
| 4248 | 2354 | 1 | 3,2680000E-02 | 3,2866667E-02 | 3,2780000E-02 | 3,2860000E-02 | 3,2960000E-02 |
| 4240 | 2358 | 1 | 2,6170000E-02 | 2,6273333E-02 | 2,6060000E-02 | 2,6260000E-02 | 2,6500000E-02 |
| 4232 | 2362 | 1 | 2,5370000E-02 | 2,5383333E-02 | 2,5330000E-02 | 2,5410000E-02 | 2,5410000E-02 |
| Proximity Index | | | Gatsche D | Gatsche D | Gatsche 3A | Gatsche 3B | Gatsche 3C |
| $\lambda$(cm-1) | $\lambda$(nm) | Loading | Measured | Estimated | $6.76 \times 10^{-6}$ | $4.6 \times 10^{-6}$ | $2.69 \times 10^{-6}$ |
| 4224 | 2367 | 1 | 2,6390000E-02 | 2,6493333E-02 | 2,6390000E-02 | 2,6520000E-02 | 2,6570000E-02 |
| 4212 | 2374 | 1 | 2,6780000E-02 | 2,6876667E-02 | 2,6850000E-02 | 2,6890000E-02 | 2,6890000E-02 |
| 4200 | 2380 | 1 | 2,7840000E-02 | 2,7633333E-02 | 2,7610000E-02 | 2,7640000E-02 | 2,7650000E-02 |
| 4192 | 2385 | 1 | 2,8190000E-02 | 2,8150000E-02 | 2,8210000E-02 | 2,8140000E-02 | 2,8100000E-02 |
| 4184 | 2390 | 1 | 2,8030000E-02 | 2,8146667E-02 | 2,8210000E-02 | 2,8030000E-02 | 2,8200000E-02 |
| 4176 | 2394 | 1 | 2,8540000E-02 | 2,8663333E-02 | 2,8730000E-02 | 2,8600000E-02 | 2,8660000E-02 |
| 4170 | 2398 | 1 | 2,8970000E-02 | 2,9000000E-02 | 2,8960000E-02 | 2,9010000E-02 | 2,9030000E-02 |
| 4160 | 2403 | 1 | 2,8410000E-02 | 2,8526667E-02 | 2,8550000E-02 | 2,8480000E-02 | 2,8550000E-02 |
| 4152 | 2408 | 1 | 2,7870000E-02 | 2,7740000E-02 | 2,7670000E-02 | 2,7760000E-02 | 2,7790000E-02 |
| 4136 | 2417 | 1 | 2,6790000E-02 | 2,6840000E-02 | 2,6860000E-02 | 2,6810000E-02 | 2,6850000E-02 |
| 4120 | 2427 | 1 | 2,5720000E-02 | 2,5660000E-02 | 2,5660000E-02 | 2,5660000E-02 | 2,5660000E-02 |

TABLE 3.1-continued

Determination of the properties of a crude paraffin

| | | | | | | | |
|---|---|---|---|---|---|---|---|
| 4104 | 2436 | 1 | 2,4570000E-02 | 2,4506667E-02 | 2,4510000E-02 | 2,4420000E-02 | 2,4590000E-02 |
| 4092 | 2443 | 1 | 2,4010000E-02 | 2,3953333E-02 | 2,3970000E-02 | 2,3910000E-02 | 2,3980000E-02 |
| 4080 | 2450 | 1 | 2,3920000E-02 | 2,4056667E-02 | 2,4130000E-02 | 2,3970000E-02 | 2,4070000E-02 |
| 4072 | 2455 | 1 | 2,4550000E-02 | 2,4480000E-02 | 2,4580000E-02 | 2,4410000E-02 | 2,4450000E-02 |
| 4068 | 2458 | 1 | 2,4530000E-02 | 2,4540000E-02 | 2,4580000E-02 | 2,4480000E-02 | 2,4560000E-02 |
| 4048 | 2470 | 1 | 2,0460000E-02 | 2,0390000E-02 | 2,0480000E-02 | 2,0240000E-02 | 2,0450000E-02 |
| 4000 | 2500 | 1 | 1,5750000E-02 | 1,5656667E-02 | 1,5660000E-02 | 1,5650000E-02 | 1,5660000E-02 |
| Density kg/l | | | 0,8901 | 0,8904 | 0,8898 | 0,8900 | 0,8915 |
| Viscosity at 100° C. sCt | | | 8,07 | 8,03 | 7,80 | 8,15 | 8,15 |
| Oil Content % | | | 28 | 27,8 | 26,9 | 25,75 | 31,0 |

Figure 1:
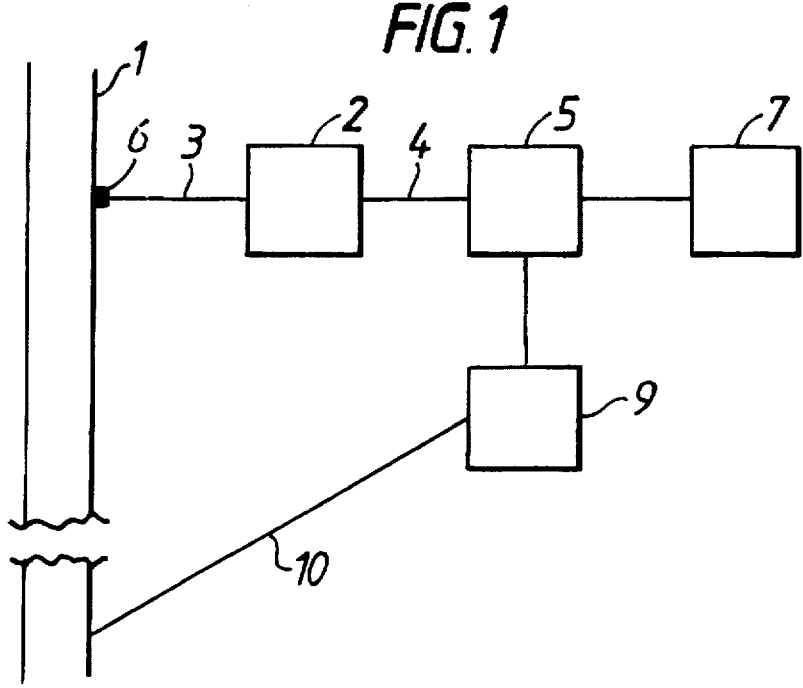
FIG. 1 represents a schematic diagram showing apparatus for use in the invention.

In FIG. 1, an optical fibre or tube 3 links a spectrometer 2 and a probe 6 in or at process line 1. The spectrophotometer 2 produces absorbance signals at more than 1 wavelength, which signals are passed via line 4 to computer 5, where thee signals as such or after conversion to one or more derivative signals, are used to enable the computer to access the databank 7 of standard absorptions and properties/yields therein. The signals are compared to those of the standard absorptions as described above and one or more standard absorption(s) and its/their corresponding property(ies) or yield(s) The output of the computer 5 may be in the form of spectral absorbancies or a property or yield of the product in line 1 and may be printed in hard copy. Preferably however, the output as a signal is used to control the process involved with the product in line 1. ie for which line 1 is a feed or a product line; in this case the computer 5 is inked to and instructs the controller 9 which, via line 10, controls that process by acting on operating conditions eg. via valves/temperature and/or pressure controls in line 1 or in relation to line 1. By this means the property or yield of product in line 1 can be optimised.

Figure 2:
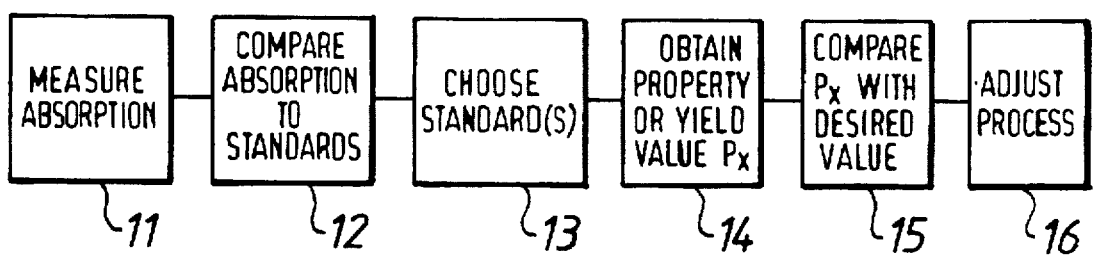
FIG. 2 represents a schematic block flow diagram for the method of the invention.

In FIG. 2, the initial operation 11 is to measure the absorption of the unknown, after which in the second step 12, the absorptions are compared to absorptions in spectra of standards, and in the third step 13, the spectra of the standards Sm are chosen according to criteria described above, and then in step 14, the property(ies) or the standard (s) Sm chosen is used to obtain the desired property or yield. If the spectrum on only 1 standard Sm is chosen, then the value $P_x$ of the unknown is the same as that of that standard Pm. If more than 1 spectrum is chosen, the value $P_x$ of the unknown is the average of the values Pm of the standards. If desired in an optional step 15, the value $P_x$ is compared to the desired value for the unknown and in step 16 the process involving the unknown is adjusted to make the value $P_x$ the same as the desired value.

We claim:

1. A method of determining or predicting a value $P_x$ of a property of a material X or a property of a product of a process from said material or yield of said process, which method comprises measuring the absorption of said material $D_{ix}$ at more than one wavelength in the region 600–2600 nm, comparing the said absorptions or a derivative thereof with absorptions $D_{im}$ or derivatives thereof at the same wavelengths for a number of standards S in a bank for which the said property is known, and choosing from the bank at least one standard $S_m$ with properties $P_m$ having the smallest average value of the absolute difference at each wavelength i between the absorption $D_ix$ (or derivative thereof) for the material and the absorption $D_im$ (or derivative thereof) for the standard $S_m$ to obtain $P_x$, with averaging of said properties or yields $P_m$, when more than one standard $S_m$ is chosen and wherein said material X is a composition comprising part of a lubricating oil fraction obtainable from a distillation of oil.

2. A method according to claim 1 wherein a proximity index is defined by $i^2(xm)=\Sigma/Dix-Dim)^2$ and is less than the minimal index $i_m$ which has been determined from the standards Sa, Sb, Sc . . . by (a) calculating for each pair of standards Sa/Sb, Sa/Sc the value of $i^2(a,b)$ etc. (b) relating the values of $i^2(a,b)$ etc to the corresponding differences EP (ab) in properties Pa, Pb etc (c) calculating for each value L for which $i^2$ (ab) is $\leq L$, the average of the corresponding differences EPab, (d) calculating Minimal index from the value of minimal index $i^2(ab)$ where average EPab is the same as reproducibility standard for the property.

3. A method according to of claim 2 wherein properties of standards and spectra for consideration for possible choice are estimated by interpolation from measured properties of Standards and spectra for which the proximity index with respect to the unknown X is not more than 10 times the Minimal Index.

4. A method according to claim 1, wherein the properties of synthetic standards, which are mixtures, and their spectra for consideration for possible choice for $S_m$ are estimated from existing standards in the bank for which, in respect of each existing standard for use in said mixture equation (4) and (5) are $$MinCj-uj \leq C_j \leq Max\ Cj+uj \quad (4)$$

and $$\Sigma Cj=1 \quad (5)$$

wherein

Cj is fraction of component 1 in the sample i

Min Cj is the minimum of j in the samples for which the method is to be used

Max Cj is the maximum of j in the samples for which the method is to be used uj is between 1.0 and 0.05.

5. A method according to claim 4 wherein at least one of (i) the estimated Standards and the corresponding spectra, and (ii) the property $P_x$ of the unknown material and its spectrum, are added the bank.

6. A method according to claim 1 wherein the property is a physicochemical property of material X.

7. A method according to claim 1 wherein the property is a physicochemical property or yield of a product of a process to which at least one material X is a feed.

8. A method according to claim 1 wherein said material comprises at least one of a lube base oil, bright stock, process oil, wax and paraffin.

9. A method according to claim 8, wherein the property is of the material, which is (i) a base oil and the property is at least one of the density, viscosity, Viscosity Index, Flash Point, Pour Point, and the content of sulphur, nitrogen base, aromatic carbon and Polycyclic aromatic hydrocarbon, (ii) a wax or paraffin or mixture thereof with a base oil and the property is at least one of the density, viscosity and base oil content or (iii) a process oil and the property is at least one of the density, clear point, viscosity and content of sulphur or polycyclic aromatic hydrocarbon.

10. A method according to claim 1 which is computer implemented.

11. Apparatus suitable for use in the method of claim 1 which comprise an NTR spectrometer receiving at least one signal from a food or product line in said process and being coupled to a computer to effect continuous measurement of the spectra of the feed and/or product and provide feed back control of the process.

12. A method according to claim 1 wherein a proximity index is defined by $i^2(xm)=\Sigma(Dix-Dim)^2$ and is less than the minimal index $i_m$ which has been determined from the standards Sa, Sb, Sc . . . by (a) calculating for each pair of standards Sa/Sb, Sa/Sc the value of $i^2(a,b)$ etc, (b) relating the values of $i^2(a,b)$ etc to the corresponding differences EP (ab) in properties Pa, Pb etc (c) calculating for each value L for which $i^2$ (ab) is $\leq L$, the average of the corresponding differences EPab, d) calculating Minimal index from the value of minimal index $i^2(ab)$ where average EPab is the same as reproducibility standard for the property and wherein the property is a physiochemical property of material x.

13. A method according to claim 1 wherein a proximity index is defined by $i^2(xm)=\Sigma(Dix-Dim)^2$ and is less than the minimal index $i_m$ which has been determined from the standards Sa, Sb, Sc . . . by (a) calculating for each pair of standards Sa/Sb, Sa/Sc the value of $i^2(a,b)$ etc, (b) relating the values of $i^2(a,b)$ etc to the corresponding differences EP (ab) in properties Pa, Pb etc (c) calculating for each value L for which $i^2$ (ab) is $\leq L$, the average of the corresponding differences EPab, (d) calculating Minimal index from the value of minimal index $i^2(ab)$ where average EPab is the same as reproducibility standard for the property and wherein the property is a physicochemical property or yield of a product of a process to which at least one material x is a feed.

14. A method according to claim 1 wherein a proximity index is defined by $i^2(xm)=\Sigma(Dix-Dim)^2$ and is less than the minimal index $i_m$ which has been determined from the standards Sa, Sb, Sc . . . by (a) calculating for each pair of standards Sa/Sb, Sa/Sc the value of $i^2(a,b)$ etc, (b) relating the values of $i^2(a,b)$ etc to the corresponding differences EP (ab) in properties Pa, Pb etc (c) calculating for each value L for which $i^2$ (ab) is $\leq L$, the average of the corresponding differences EPab, d) calculating Minimal index from the value of minimal index $i^2(ab)$ where average EPab is the same as reproducibility standard for the property and wherein said material comprises at least one of a lube base oil, bright stock, proceco oil, wax and paraffin.

15. A method according to claim 1 wherein a proximity index is defined by $i^2(xm)=\Sigma(Dix-Dim)^2$ and is less than the minimal index $i_m$ which has been determined from the standards Sa, Sb, Sc . . . by (a) calculating for each pair of standards Sa/Sb, Sa/Sc the value of $i^2(a,b)$ etc, (b) relating the values of $i^2(a,b)$ etc to the corresponding differences EP (ab) in properties Pa, Pb etc (c) calculating for each value L for which $i^2$ (ab) is $\leq L$, the average of the corresponding differences EPab, (d) calculating Minimal index from the value of minimal index $i^2(ab)$ where average EPab is the same as reproducibility standard for the property and wherein the property is of the material, which is (i) a base oil and the property is at least one of the density, viscosity, Viscosity Index, Plash Point, Pour Point, and the content of sulphur, nitrogen base, aromatic carbon and Polycyclic aromatic hydrocarbon, (ii) a wax or paraffin or mixture thereof with a base oil and the property is at least one of the density, viscosity and base oil content or (iii) a process oil and the property is at least one of the density, clear point, viscosity and content of sulphur or polycyclic aromatic hydrocarbon.

16. The method according to claim 1 wherein the property is a physicochemical property of material x and wherein said material comprises at least one of lube base oil, bright stock, proceco oil, wax and paraffin.

17. The method according to claim 1 wherein the property is a physicochemical property of material x and wherein the property is of the material, which is (i) a base oil and the property is at least one of the density, viscosity, Viscosity Index, Flash Point, Pour Point, and the content of sulphur, nitrogen base, aromatic carbon and Polycyclic aromatic hydrocarbon, (ii) a wax or paraffin or mixture thereof with a base oil and the property is at least one of the density, viscosity and base oil content or (iii) a process oil and the property is at least one of the density, clear point, viscosity and content of sulphur or polycyclic aromatic hydrocarbon.

18. The method according to claim 1 wherein the property is a physicochemical property or yield of a product of a process to which at least one material x is a feed and wherein said material comprises at least one of lube base oil, bright stock, proceco oil, wax and paraffin.

19. The method according to claim 1 wherein the property is a physicochemical property or yield of a product of a process to which at least one material x is a feed and wherein the property is of the material, which is (i) a base oil and the property is at least one of the density, viscosity, Viscosity index, Flash Point, Pour Point, and the content of sulphur, nitrogen base, aromatic carbon and Polycyclic aromatic hydrocarbon, (ii) a wax or paraffin or mixture thereof with a base oil and the property is at least one of the density, viscosity and base oil content or (iii) a process oil and the property is at least one of the density, clear point, viscosity and content of sulphur or polycyclic aromatic hydrocarbon.

20. A method according to claim 1 wherein a proximity index is defined by $i^2(xm)=\Sigma(Dix-Dim)^2$ and is less than the minimal index $i_m$ which has been determined from the standards Sa, Sb, Sc . . . by (a) calculating for each pair of standards Sa/Sb, Sa/Sc the value of $i^2(a,b)$ etc, (b) relating the values of $i^2(a,b)$ etc to the corresponding differences EP (ab) in properties Pa, Pb etc (c) calculating for each value L for which $i^2$ (ab) is $\leq L$, the average of the corresponding differences EPab, (d) calculating Minimal index from the value of minimal index $i^2(ab)$ where average EPab is the same as reproducibility standard for the property, wherein the property is a physicochemical property of material x and wherein said material comprises at least one of lube base oil, bright stock, proceco oil, wax and paraffin.

21. The method according to claim 20 wherein the property is of the material which is a base oil and the property is at least one of the density, viscosity, Viscosity Index, Flash Point, Pour Point and the content of sulphur, nitrogen base, aromatic carbon and Polycyclic aromatic hydrocarbon.

22. The method according to claim 20 wherein the property is of the material which is a wax or paraffin or mixture thereof with a base oil and the property is at least one of the density, viscosity and base oil content.

23. The method according to claim 20 wherein the property is of the material which is a process oil and the property is at least one of the density, clear point, viscosity and content of sulphur or polycyclic aromatic hydrocarbon.

24. A method according to claim 1 wherein a proximity index is defined by $i^2(xm)=\Sigma(Dix-Dim)^2$ and is less than the minimal index $i_m$ which has been determined from the standards Sa, Sb, Sc . . . by (a) calculating for each pair of standards Sa/Sb, Sa/Sc the value of (a,b) etc, (b) relating the values of $i^2(a,b)$ etc to the corresponding differences EP (ab) in properties Pa, Pb etc (c) calculating for each value L for which $i^2$ (ab) is $\leq L$, the average of the corresponding differences EPab, (d) calculating Minimal index from the value of minimal index $i^2(ab)$ where average EPab is the same as reproducibility standard for the property, wherein the property is a physicochemical property or yield of a product of a process to which at least one material x is a feed and wherein said material comprises at least one of lube base oil, bright stock, proceco oil, wax and paraffin.

25. The method according to claim 24 wherein the property is of the material which is a base oil and the property is at least one of the density, viscosity, Viscosity Index, Flash Point, Pour Point and the content of sulphur, nitrogen base, aromatic carbon and Polycyclic aromatic hydrocarbon.

26. The method according to claim 24 wherein the property is of the material which is a wax or paraffin or mixture thereof with a base oil and the property is at least one of the density, viscosity and base oil content.

27. The method according to claim 24 wherein the property is of the material which is a process oil and the property is at least one of the density, clear point, viscosity and content of sulphur or polycyclic aromatic hydrocarbon.

28. A computer to perform the method of determining or predicting a value $P_x$ which is a value of a property of a material X or a property of a product of a process from said material or yield of said process, which method comprises measuring the absorption $D_{ix}$ of said material at more than one wavelength in the region 600–2600 nm, comparing the said absorptions or a derivative thereof with absorptions $D_{im}$ or derivatives thereof at the same wavelength for a number of standards S in a bank for which the said property of yield P is known, and choosing from the bank at least one standard $S_m$ with property $P_m$ said standard having the smallest average value of the absolute difference at each wavelength i between the absorption $D_ix$ (or derivative thereof) for the material and the absorption $D_im$ (or derivative thereof) for the standard $S_m$ to obtain $P_x$, with averaging of said properties or yields $P_m$ when more than one standard $S_m$ is chosen wherein said material X is a composition comprising part of a lubricating oil fraction obtainable from a distillation of oil.

* * * * *

UNITED STATES PATENT AND TRADEMARK OFFICE
CERTIFICATE OF CORRRECTION

Page 1 of 3

PATENT NO. : 5,740,073
DATED : April 14, 1998
INVENTOR(S) : Bages et al.

It is certified that error appears in the above-identified patent and that said Letters Patent is hereby corrected as shown below:

On the title page, in item [56] under Other Publications insert the followings:

OTHER DOCUMENTS

| | | |
|---|---|---|
| | | O. U. Anders, "Ratio Matching - A Statistical Aid for Discovering Generic Relationships among Samples," Analytical Chemistry (Oct. 1972), 44, pp. 1930-1933. |
| | | C. W. Brown, et al., "Infrared Analysis of Weathered Petroleum Using Vacuum Techniques," Analytical Chemistry (Jan. 1976), 48, pp. 191-195. |
| | | A. J. Martens, et al., "Test Olefin Feed by Micropyrolysis," Hydrocarbon Processing (April 1979), pp. 199-202. |
| | | J. J. Royer, "Proximity Analysis: A Method for Multivariate Geodata Processing, Application to Geochemical Processing," Sci. Terre, Serl: Inf. Geol. (April 1984), 20, pp. 223-243. |
| | | H. A. M. Rasheed, et al., "Identification of Petroleum Products by the Ratio Matching Method," Journal of Petroleum Research (1986), 5, pp. 1-17. |
| | | M. A. Puskar, et al., "Infrared Screening Technique for Automated Identification of Bulk Organic Mixtures," Analytical Chemistry (Aug. 1986), 58, pp. 1981-1989. |
| | | H. A. M. Rashid, et al., "Gasoline Analysis Using Gas Liquid Chomatography and Ratiomatching for Quality Control," Journal of Petroleum Research (1988), 7, pp. 169-179. |
| | | B. Descales, et al., "Determination of Research and Motor Octane Numbers (RON and MON) of Gasolines by the Near Infra Red (NIR) Method," Pet. Tech. (1989), 349, pp. 2-8. |
| | | H. A. Rashid, et al., "Determination of Several Physical Properties of Light Petroleum Products Using IR," Fuel Science and Technology Int'l. (1989), 7, pp. 237-250. |

UNITED STATES PATENT AND TRADEMARK OFFICE
CERTIFICATE OF CORRRECTION

PATENT NO. : 5,740,073  
DATED : April 14, 1998  
INVENTOR(S) : Bages et al.

Page 2 of 3

It is certified that error appears in the above-identified patent and that said Letters Patent is hereby corrected as shown below:

OTHER DOCUMENTS

| | | |
|---|---|---|
| | | A. Martens, et al., "NIR Process Control of a Steam Cracker," Int. Conf. Near Infrared Spectrosc. (1991), pp. 447-481. |
| | | S. Kokot, et al., "Application of FT-IR Spectroscopy for the Prediction of Properties of Australian Refined Petroleum Products," Proc. SPIE-Int. Soc. Opt. Eng. (1992), 1575, pp. 195-196. |
| | | J. M. McDonald, et al., "Gasoline Blending Using NIR Spectroscopy and LP Optimization," NPRA Computer Conf. (1992), CC-92-137, pp. 1-9. |
| | | S. J. Swarin, et al., "Predicting Gasoline Properties Using Near-IR Spectroscopy Beyond Octane Numbers and Hydrocarbon Classes," Spectroscopy (Sept. 1992), 7, pp. 42-49. |
| | | B. Descales, et al., "Analyse en ligne sur des unites petrochimiques par spectrophotometrie proche infrarouge," Analysis (1993), 23, pp. M25-M28. |
| | | I. Cermelli, et al., "On Line Near Infrared Analysis Applications in Petrochemistry," Near Infrared Spectroscopy, Harwood, New York, (1992), pp.395-400. |
| | | S. M. Maggard, et al., "The Advantage of Blending Reformulated Fuels Using Near Infrared Octane and Combustion Analysis with Closed Loop Feedback," Proc.-Annu. Symp. Instr. Process Ind. (1993), 48, pp. 61-67. |
| | | J. Workman, Jr., "Review of Process Near Infrared Spectroscopy: 1980-1994," Near Infrared Spectrosc. (1993), 1, pp. 221-245. |
| | | J. Coates, "New Analyser Technology to Monitor Refinery Unit Production Efficiency," Hydrocarb. Technol. Int. (1994), pp. 193-197. |

UNITED STATES PATENT AND TRADEMARK OFFICE
CERTIFICATE OF CORRECTION

PATENT NO. : 5,740,073
DATED : April 14, 1998
INVENTOR(S) : Bages et al.

It is certified that error appears in the above-identified patent and that said Letters Patent is hereby corrected as shown below:

OTHER DOCUMENTS

| | | |
|---|---|---|
| | | T. Zerlia, "Spettroscopia del vicino infrarosso (NIR) per l'esame di prodotti petroliferi," |
| | | Riv. Combust. (Sept. 1994), 48, pp. 349-354. |
| | | Y. Yamamoto, et al., Idemitsu Giho (1994), 37, pp. 608-615. |
| | | |
| | | D. Lambert, et al., "Optimize Stream Cracking with Online NIR Analysis." |
| | | Hydrocarbon Processing (Dec. 1995), pp. 103-108. |

Signed and Sealed this

Twenty-third Day of February, 1999

Attest:

Q. TODD DICKINSON

*Attesting Officer*     *Acting Commissioner of Patents and Trademarks*